(12) United States Patent
Garst et al.

(10) Patent No.: US 7,115,748 B2
(45) Date of Patent: Oct. 3, 2006

(54) METHOD OF MAKING IMIDAZOLE-2-THIONES

(75) Inventors: Michael E. Garst, Newport Beach, CA (US); Lloyd Jay Dolby, Eugene, OR (US); Shervin Esfandiari, Eugene, OR (US); Alfred Arthur Avey, Jr., Eugene, OR (US)

(73) Assignee: Allergan, Inc., Irvine, CA (US)

( * ) Notice: Subject to any disclaimer, the term of this patent is extended or adjusted under 35 U.S.C. 154(b) by 115 days.

(21) Appl. No.: 11/007,454

(22) Filed: Dec. 7, 2004

(65) Prior Publication Data

US 2006/0122400 A1    Jun. 8, 2006

(51) Int. Cl.
*C07D 233/42* (2006.01)
(52) U.S. Cl. .................................. 548/325.1
(58) Field of Classification Search ............. 548/322.5, 548/325.1
See application file for complete search history.

(56) References Cited

FOREIGN PATENT DOCUMENTS

DE          3717254     * 11/1987

OTHER PUBLICATIONS

Takikawa et al. Chemistry Letters, 1982, 641-642.*
Reynaud et al. Journal of Heterocyclic Chemistry, 1980, 17(8), 1789-92. Cas Abstract and Reactions Attached.*
Chowdhury et al. Pakistan Journal of Scientific and Industrial Research, 2001, 44(2), 63-66. Cas Abstract and Reactions Attached.*
Zhivotova et al. Izvestiya Natsional'noi Akademii Nauk Respubliki Kazakhstan, Seriya Khimicheskaya 2004, 4, 31-33. Cas Abstract and Reactions Attached.*
Thijssen et al. Journal of Labelled Compounds and Radiopharmaceuticals, 1987, 24(7), 779-86. Cas Abstract and Reactions attached*
Davies et al. Tetrahedron, 1993, 49(20), 4419-38. Cas Abstract and Reaction Attached.*
Nicolaou et al. Agnew. Chem. Int. Ed., 2003, 42, 4077-4082.*
Gust et al. Arch. Pharm. Pharm. Med. Chem. 2001, 93-100.*
Bylund et al, "IV. International Union of Pharmacology Nomenclature of Adrenoceptors", Pharmacol Rev. 46, pp. 121-136 (1994).
Mohanta et al, "1-(Methyldithiocarbonyl)imidazole: a Synthesis of Substituted Thioureas" Tetrahedron, vol. 56, No. 4, Jan. 2001, pp. 629-637, XP004186122.
Jones et al, "Studies on Imidazoles. IV. The synthesis and Antithyroid Activity of Some I-Substituted-2-mercaptoimidazoles", Journal of the American Chemical Society, vol. 71, 1949, pp. 4000-4002, XP002374390.

* cited by examiner

*Primary Examiner*—Joseph K. McKane
*Assistant Examiner*—Jason M. Nolan
(74) *Attorney, Agent, or Firm*—Robert Baran; Brent Johnson; Martin Voet

(57) ABSTRACT

The present invention provides a method of making an imidazole-2-thione which comprises the steps of reacting a vicinal diamine with a compound having a thiocarbonyl moiety and oxidizing the resulting reaction product to obtain said imidazole-2-thione.

8 Claims, No Drawings

METHOD OF MAKING IMIDAZOLE-2-THIONES

BACKGROUND OF THE INVENTION

1. Field of the Invention

This invention relates to a method of making imidazole-2-thiones. Imidazole-2-thiones may have pharmaceutical activity or may be used to synthesize compounds having pharmaceutical activity, e.g. adrenergic activity, e.g. alpha 2 adrenergic activity.

2. Background of the Art

Compounds which have adrenergic activity are well known in the art, and are described in numerous United States and foreign patents and in scientific publications. It is generally known and accepted in the art that adrenergic activity is useful for treating animals of the mammalian species, including humans, for curing or alleviating the symptoms and conditions of numerous diseases and conditions. In other words, it is generally accepted in the art that pharmaceutical compositions having an adrenergic compound or compounds as the active ingredient are useful for treating glaucoma, chronic pain, nasal congestion, high blood pressure, congestive heart failure and inducing anesthesia.

The two main families of adrenergic receptor are termed alpha adrenergic receptors and beta adrenergic receptors in the art, and each of these two families is known to have subtypes, which are designated by letters of the alphabet, such as α2A, α2B. See the article by Bylund et al, *Pharmacol Rev.* 46, pp. 121–136(1994).

SUMMARY OF THE INVENTION

The present invention provides a method of making an imidazole-2-thione which comprises the steps of reacting a vicinal diamine having the formula I

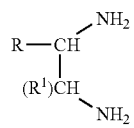

wherein R is hydrogen, alkyl, alkenyl, alkoxy, carbocyclic aryl and heterocyclic aryl radicals and $R^1$ is selected from the group consisting of hydrogen, alkyl, alkenyl, alkoxy, carbocyclic aryl and heterocyclic aryl radicals with a compound having a thiocarbonyl moiety to obtain a first reaction product having the general formula II

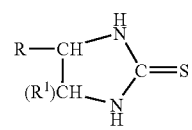

and oxidizing said reaction product to obtain an imidazole-2-thione having the formula III

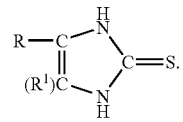

Preferably $R^1$ is hydrogen.

Preferably R is selected from the group consisting of hydrocarbyl radicals having from one to twenty carbon atoms and single ring heteroaryl radicals wherein the heteroatom is selected from the group consisting of oxygen and sulfur.

More preferably, R is selected from the group consisting of alkyl, aryl, alkenyl, furyl and thienyl radicals, e.g. benzyl, phenyl, phenyl ethyl, cyclohexene, 3-pentyl, 2-pentyl, butyl, 2-furyl and 2-thienyl radicals.

Preferably said compound having a thiocarbonyl moiety is selected from the group consisting of 1, 1' thiocarbonyl diimidazole and alkyl isothiocyanate.

In the method of the present invention said first reaction product may be reacted with $R^3$—Cl to provide a second reaction product having the formula IV

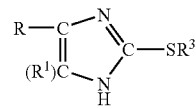

wherein $R^3$ is a suitable protecting group and said second reaction product is oxidized to provide said imidiazole-2-thione.

Preferably said protecting group is selected from the group consisting of allyl, benzyl, 2, 4 dimethoxy benzyl, 2 methoxybenzyl and acetoxybenzyl.

The vicinal diamine may prepared by reacting a compound having formula V

wherein R is selected from the group consisting of hydrogen, alkyl, alkenyl, alkoxy, carbocyclic aryl and heterocyclic aryl radicals, with nitromethane to obtain a reaction product of formula VIII

and said reaction product of formula VIII is reacted with O-methylhydroxylamine to obtain a reaction product of formula IX

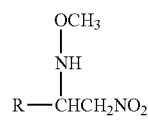

and said reaction product of formula IX is reduced to a vicinal diamine having the
formula VII

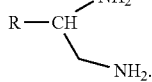

Preferably, the reaction product having the formula VI is reduced with diisobutyl aluminum hydride to obtain said vicinal diamine of formula VII.

Alternatively, said vicinal diamine may be prepared by reacting a compound of formula V

with nitromethane to obtain a reaction product of formula VIII

said reaction product of formula VIII is reacted with O-methylhydroxylamine to obtain a reaction product of formula IX

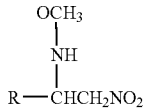

and said reaction product of formula IX is reduced to a vicinal di amine having the formula VII

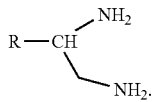

The imidazole-2-thione prepared by the method of the present invention is a tautomeric structure. Thus, the compound of formula III may be represented as

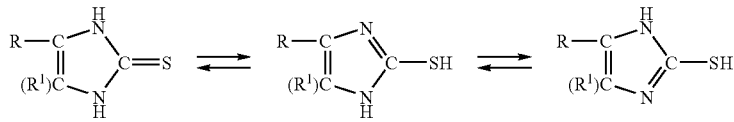

DETAILED DESCRIPTION OF THE INVENTION

The following defined terms are used throughout this specification:

"Me" refers to methyl.
"Et" refers to ethyl.
"tBu" refers to t-butyl.
"iPr" refers to i-propyl.
"Ph" refers to phenyl.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, $=O$, $=S$, $NO_2$, halogen, dimethyl amino, and SH.

"Alkenyl" refers to a straight-chain, branched or cyclic unsaturated hydrocarbon group containing at least one carbon-carbon double bond. Preferably, the alkenyl group has 1 to 12 carbons. More preferably it is a lower alkenyl of from 1 to 7 carbons, most preferably 1 to 4 carbons. The alkenyl group may be optionally substituted with one or more substituents selected from the group consisting of hydroxyl, cyano, alkoxy, $=O$, $=S$, $NO_2$, halogen, dimethyl amino, and SH.

"Alkynyl" refers to a straight-chain, branched or cyclic unsaturated hydrocarbon containing at least one carbon-carbon triple bond. Preferably, the alkynyl group has 1 to 12 carbons. More preferably it is a lower alkynyl of from 1 to 7 carbons, most preferably 1 to 4 carbons. The alkynyl group may be optionally substituted with one or more substituents selected from the group consisting of hydroxyl, cyano, alkoxy, $=O$, $=S$, $NO_2$, halogen, dimethyl amino, and SH.

"Alkoxyl" refers to an "O-alkyl" group.
"Dibal" refers to diisobutylaluminum.
"Im" refers to imidazole
"DMSO" refers to dimethylsulfoxide.
"THF" refers to tetrahydrofuran.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino.

"Alkaryl" refers to an alkyl that is covalently joined to an aryl group. Preferably, the alkyl is a lower alkyl.

"Carbocyclic aryl" refers to an aryl group wherein the ring atoms are carbon.

"Heterocyclic aryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Amide" refers to —C(O)—NH—R', wherein R' is alkyl, aryl, alkylaryl or hydrogen.

"Thioamide" refers to —C(S)—NH—R', wherein R' is alkyl, aryl, alkylaryl or hydrogen.

"Amine" refers to a —N(R")R'" group, wherein R" and R'" are independently selected from the group consisting of alkyl, aryl, and alkylaryl.

"Thioether" refers to —S—R", wherein R" is alkyl, aryl, or alkylaryl.

"Sulfonyl" refers to —S(O)$_2$—R"", where R"" is aryl, C(CN)=C-aryl, CH$_2$CN, alkyaryl, sulfonamide, NH-alkyl, NH-alkylaryl, or NH-aryl.

The preparation of imidazole-2-thiones according to the method of the invention is outlined below. The key steps are formation of the heterocyclic ring from a vicinal diamine and 1,1'-thiocarbonyldiimidazole and the oxidation of the resulting 2-imidazolidinethione to the corresponding imidazole-2-thione. The sulfur may be protected and the required double bond may be introduced with a Swern oxidation. As shown below, three different benzyl groups and allyl have been examined as protecting groups. The p-methoxybenzyl, p-acetoxybenzyl and allyl compounds may be deprotected in reasonable yield. In one embodiment of the method of the present invention, the imidazole-2-thione is prepared according to the following scheme: (The numbers correspond to the numbers identifying the same compounds in the Examples.)

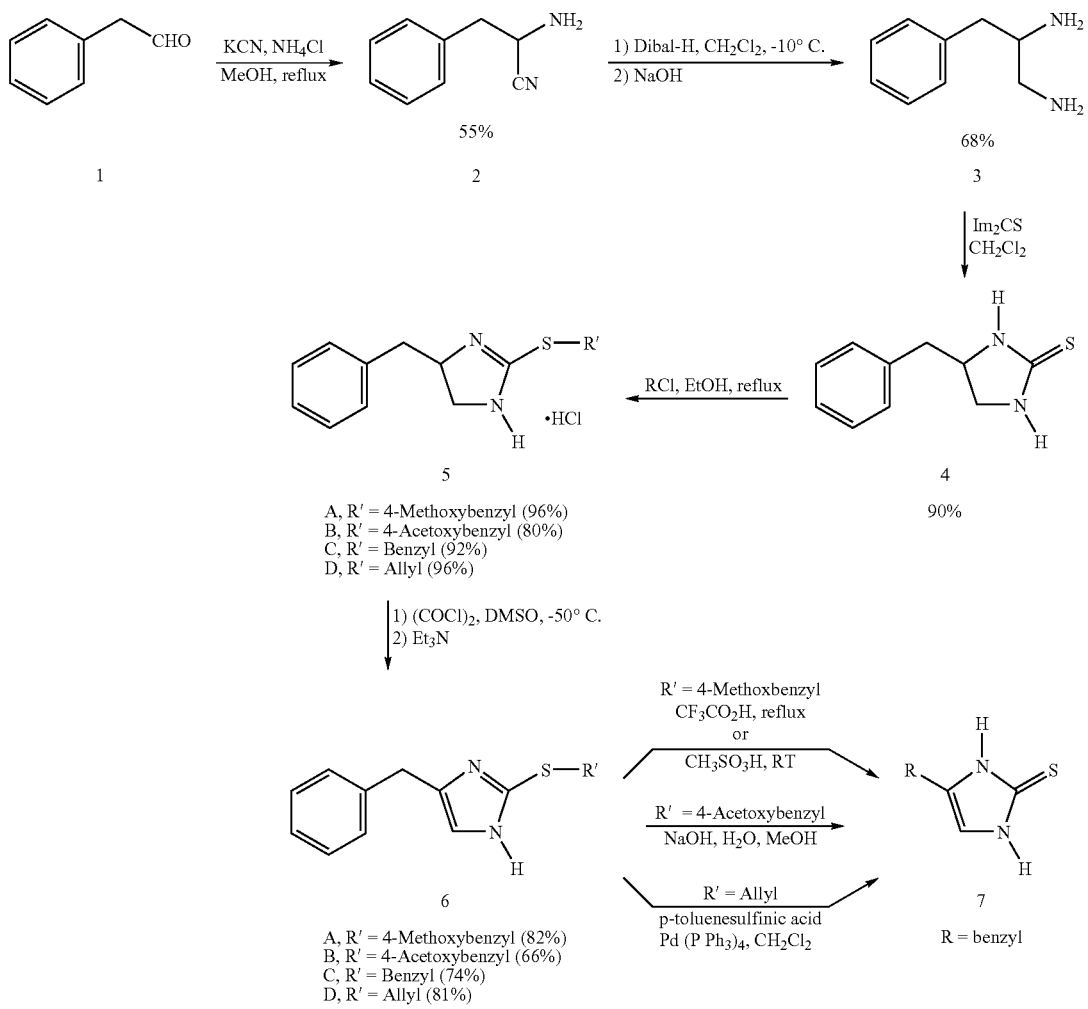

The first step of the sequence, the Strecker synthesis[2] with phenylacetaldehyde, gave 55% yields of the amino nitrile 2. Other suitable aldehydes, to be used in the synthesis, will be selected according to the choice of the R substituent on the resulting imidazole-2-thione. The reaction product is easily purified by extraction.

Dibal reduction of 2-amino-3-phenylpropanenitrile 2, gave 3-phenyl-1,2-diaminopropane 3 in 68% yield after distillation. Dibal was the best of several reducing agents that were tried for the reduction of 2-aminonitriles.

Other suitable reducing agents include lithium aluminum hydride. Treatment of 3-phenyl-1,2-diaminopropane with 1,1'-thiocarbonyldiimidazole rapidly produced 4-benzyl-2-imidazolidinethione 4. The yield was 90%, which is essentially quantitative since the starting material was about 90% pure. Most of the 2-imidazolidinethiones were prepared in good yields with 1,1'-thiocarbonyldiimadazole. However, the less expensive allyl isothiocyanate was also found to be an excellent reagent for the conversion of vicinal diamines to 2-imidazolidinethiones. The parent compound, 2-imidazolidinethione, was obtained in 91% yield from 1,2-diaminoethane and allyl isothiocyanate in refluxing bromobenzene. These conditions converted 2-thienyl-1,2-diaminoethane to the corresponding 2-imidazolidinethione, 36J, in 83% yield.

It is preferable to protect the sulfur before oxidation. Benzyl chloride, p-methoxybenzyl chloride, p-acetoxybenzyl chloride and allyl chloride all alkylated sulfur in good yield. Swern oxidation of the resulting isothiouronium salts gave the protected imidazole derivatives in yields up to 82%. The known 4-benzylimidazole-2-thione 7 was obtained by deprotecting the p-methoxybenzyl derivative with acid, the p-acetoxybenzyl derivative with base and the allyl derivative with p-toluenesulfinic acid in the presence of a catalytic amount of tetrakis (triphenylphosphine)palladium [Pd(PPh$_3$)$_4$].

Another target compound, 4-(1-phenylethyl)imidazole-2-thione 15, was prepared similarly as shown in the reaction scheme below.

All steps in this scheme worked well as in the first scheme.

Several other substituted imidazole-2-thiones were made as shown in the below reaction scheme.

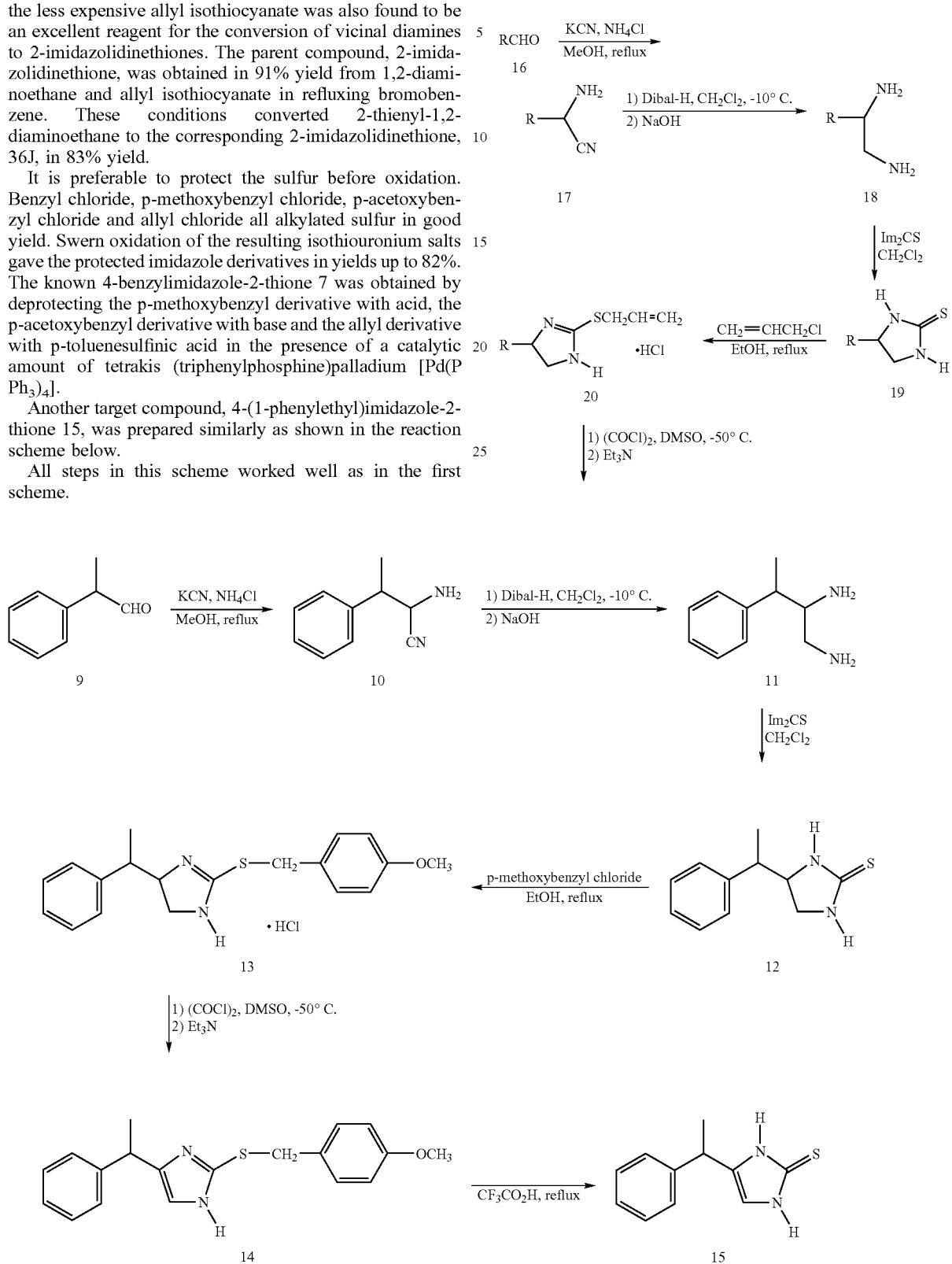

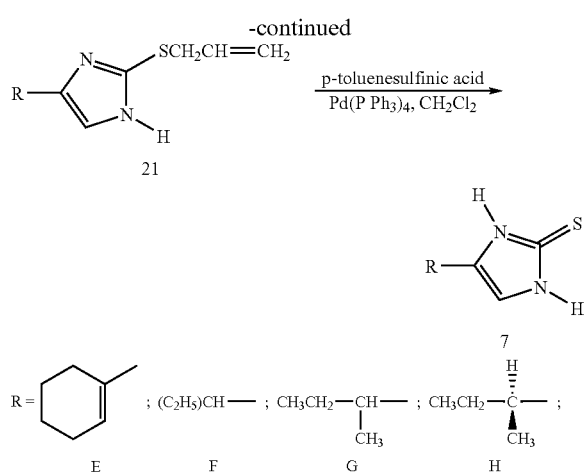

-continued

Allyl chloride was used for protecting the sulfur before oxidation for all of these examples. Racemic 4-(2-butyl) imidazole-2-thione 7G was prepared from racemic 2-ethylbutanal by this approach. The synthesis was repeated with optically active 2-methylbutanal to show that an aldehyde with a chiral carbon adjacent to the carbonyl leads to an enantiomerically enriched imidazole-2-thione. The chiral aldehyde was obtained in 61% yield by oxidizing (S)-(−)-2-methyl-1-butanol with oxalyl chloride and DMSO at −50° C. The Strecker reaction followed by Dibal-H reduction gave desired diamine 18H in 21% yield for two steps. Treatment with 1,1′-thiocarbonyldiimidazole, protecting the sulfur with allyl chloride followed by Swern oxidation gave 21H in 56% yield for three steps. The desired imidazole-2-thione 7H was obtained in 40% yield by deprotecting 21H with p-toluenesulfinic acid in the presence of a catalytic amount of Pd(P Ph$_3$)$_4$. Hplc analysis showed an enantiomeric ratio of 98:2 indicating scant racemization through the several steps.

The known 4-phenylimidazole-2-thione 31was made as shown in the reaction scheme below. Another approach to the preparation of vicinal diamines was examined to complement the Strecker synthesis-reduction sequence. The required 2-phenyl-1,2-diaminoethane was prepared by the Strecker synthesis reduction sequence and a route beginning with the condensation of benzaldehyde with nitromethane. The resulting β-nitrostyrene was condensed with O-methylhydroxylamine and hydrogenated to give 2-phenyl-1,2-diaminoethane in 74% overall yield from benzaldehyde.

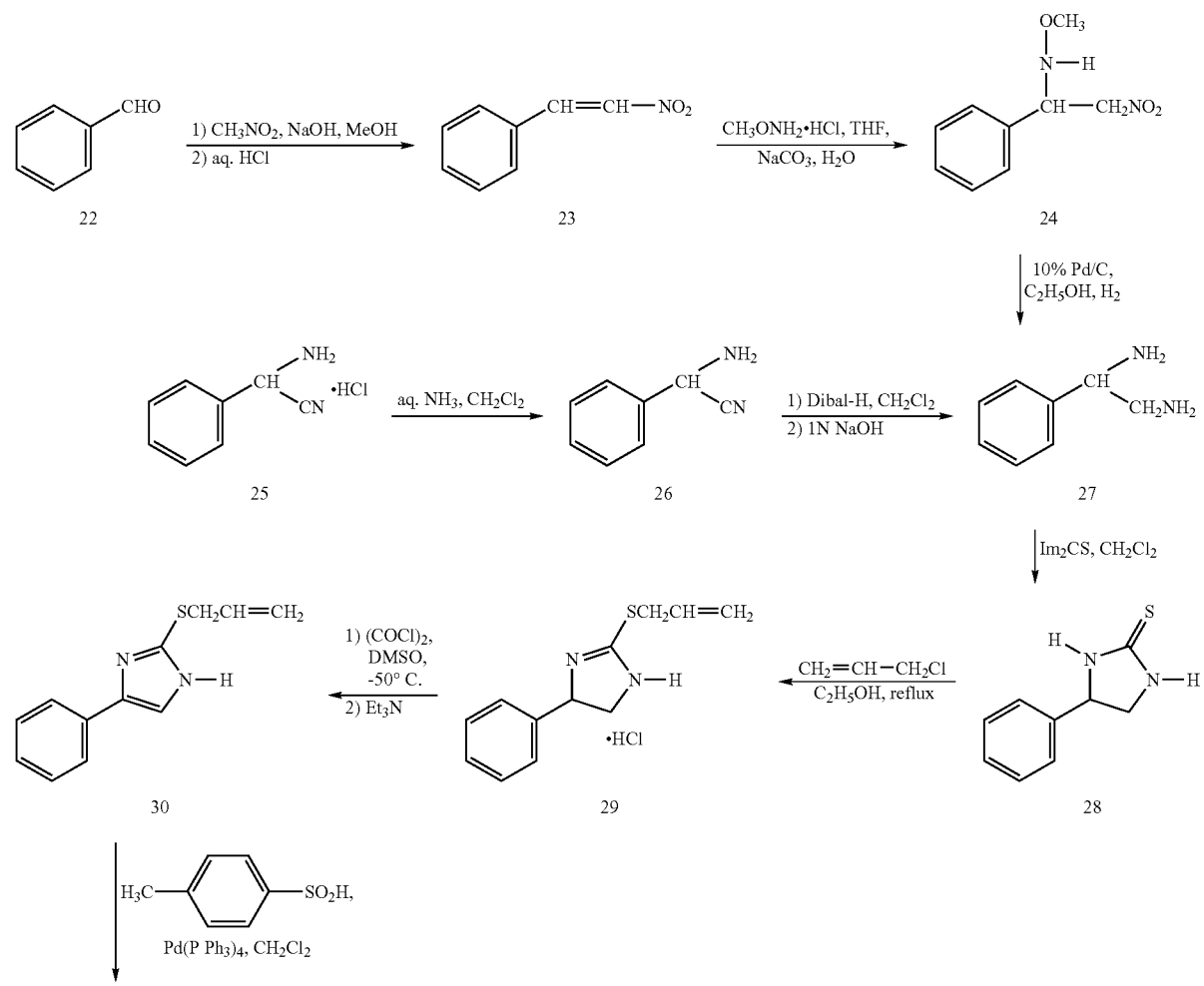

31

The furan and thiophene derivatives may be prepared by employing the 2-aryl-1-nitroethylene intermediated.

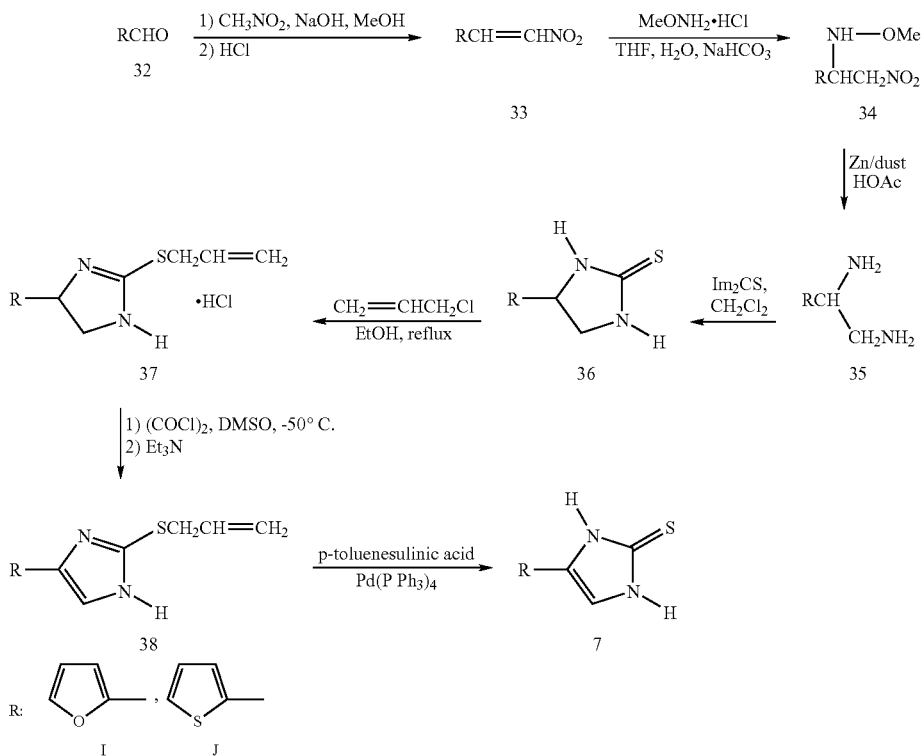

Both 2-furaldehyde, 32I, and 2-thiophenecarboxaldehyde, 32J, were condensed with nitromethane in methanol with aqueous sodium hydroxide followed by dehydration with aqueous hydrochloric acid to give corresponding 2-nitrovinyl derivatives 33I and 33J. The nitroamine derivatives 34I and 34J were readily reduced to the corresponding 1,2-diamines, 35I and 35J, with zinc dust in acetic acid. The remaining steps for formation of 4-(2-furyl)imidazole-2-thione 7I and 4-(2-thienyl)imidazole-2-thione 7J were the same as for previous examples.

The invention is illustrated by the following examples which are illustrative of a specific mode of practicing the invention and are not intended as limiting the scope of the approved claims.

EXAMPLE 1

3-Phenyl-2-aminopropanenitrile 2. In a 1L 5-necked flask equipped with a mechanical stirrer, thermometer, condenser and a dropping funnel was placed potassium cyanide (71.5 g, 1.1 mol) in water (325 mL). Ammonium chloride (64.2 g, 1.2 mol) was added. The resulting mixture was stirred to get a homogenous solution. A solution of phenylacetaldehyde (132 g of 90% purity, 1.0 mol) in methanol (325 mL) was added over 60 min. The resulting mixture was heated at 60° C. HPLC analysis indicated that the reaction was complete after 4 hr. The reaction mixture was cooled to room temperature and then dichloromethane (250 mL) and water (259 mL) were added. The aqueous layer was separated and extracted with dichloromethane (250 mL). The combined organic layers were washed with water (1×100 mL), and product was extracted with 2N HCl (2×300 mL). The combined acidic layers were back washed with dichloromethane (1×250 mL). Dichloromethane (250 mL) was added to the aqueous acidic layer after which the mixture was cooled in an ice-water bath and basified with concentrated ammonia (150 mL). The organic layer was separated and the aqueous layer was extracted with dichloromethane (2×100 ml). The organic layers were combined and washed with water (1×100 mL) then with brine (1×100 mL) and dried over anhydrous magnesium sulfate (15 g). The magnesium sulfate was filtered and the solution was evaporated under reduced pressure to give 80 g (55% yield) of the aminonitrile 2 as an oil. The oil solidified on standing in the refrigerator overnight. HPLC analysis showed a purity of 99%. NMR (CDCl$_3$) δ 7.5 (s, 5H), 3.7–4.1 (m, 1H), 3.05 (d, 2H), 1.7 (s br, 2H).

EXAMPLE 2

3-Methyl-3-phenyl-2-aminopropanenitrile 10, NMR (CDCl$_3$) δ 7.3–7.6(m, 5H), 3.6–4.1(m, 1H), 2.8–3.4(m, 1H), 1.6(S, 3H), 1.5(S, 2H), was prepared (50% yield) as described above.

EXAMPLE 3

2-(Cyclohex-1-enyl)-2-aminoethanenitrile 17E. In a flask fitted with a mechanical stirrer, a condenser and a dropping funnel was place potassium cyanide (8.45 g, 0.13 mol) and ammonium chloride (7.65 g, 0.143 mol) in water (40 mL). To this solution was added 25 mL of concentrated ammonia. A solution of cyclohex-1-enecarboxaldehyde (14.3 g, 0.13 mol) in ether (100 mL) was added at room temperature with vigorous stirring. Stirring was continued for 3 days and then the layers were separated and the aqueous layer was extracted with ether (50 mL). The combined ether layers were washed with brine (50 mL) and evaporated under reduced pressure to give 15.5 g of an oil. The oil was dissolved in dichloromethane (100 mL) and extracted with 3 M hydrochloric acid (3×30 mL). The acidic extracts were cooled in an ice bath and basified with 75 mL of concentrated ammonia solution. Extraction with dichloromethane (50 mL) afforded 7.8 g (44%) of the title compound as an oil. NMR (CDCl$_3$) δ 6.0–6.3(s br, 1H), 4.0–4.4(S br, 1H), 2.0–2.4(m, 4H), 1.3–2.0(m, 4H),

EXAMPLE 4

(±)-3-Ethyl-2-aminopentanenitrile 17F, NMR (CDCl$_3$) δ 3.8–4.0(m, 1H), 1.2–2.0(m, 5H), 0.6–1.2(m, 8H), was prepared from 2-ethylbutanal as described for 17E (32%). In this experiment 70 mL of 28% ammonia solution was used for each mole of aldehyde.

EXAMPLE 5

(±)-3-methyl-2-aminopentanenitrile 17G, NMR (CDCl$_3$) δ 3.5–3.8(S br, 1H), 0.7–2.0(m, 11H), was prepared as described for 17E (68%). In this experiment for each mole of aldehyde was used 70 mL of 28% ammonia solution.

EXAMPLE 6

(3S)-3-methyl-2-aminopentanenitrile 17H, NMR (CDCl$_3$) δ 3.4–3.8(S br, 1H), 0.6–2.2(m, 11H), was prepared as described for 17G (64%). Aldehyde 16H was made from (S)-(−)-2-methyl-1-butanol by Swern oxidation according to the following procedure.

EXAMPLE 6A (S)-(+)-2-Methylbutanal 16H. In a 500 mL 3-necked flask equipped with a thermometer, a dropping funnel, and stir-bar was placed oxalyl chloride (180 mL of 2 M solution in dichloromethane, 0.36 mol).under Argon. The solution was stirred and cooled to −50° C. A solution of dimethyl sulfoxide (56.12 g, 0.72 mol) in 50 mL of dichloromethane was added at such a rate to maintain internal temperature around −45 to −50° C. The resulting mixture was stirred at −50° C. for 45 min and then a solution of (S)-(−)-2-methyl-1-butanol (21.12 g, 0.24 mol) in 50 mL of dichloromethane was added at such a rate to maintain internal temperature between −45 t0 −50° C. After stirring for an additional 45 min at −50° C., to the reaction mixture was added N,N-diisopropylethylamine (92.88 g, 0.72 mol) in one portion. After 15 min, the cooling bath was removed. The resulting mixture was stirred at room temperature for 15 min, and then was washed with water (3×50 mL), brine (1×100 mL), and filtered through 1PS filter paper. The organic phase was dried over anhydrous magnesium sulfate (2 g) and then distilled at atmospheric pressure through a 40 cm Vigreux column to give 12.6 g (61% yield) of 16H as a colorless oil, bp 90–92° C. NMR (CDCl$_3$) δ 10.0 (s, 1H), 2.1–2.6(m, 1H), 1.3–2.1(m, 2H), 1.2 (S, 3H), 1.0 (d, 3H).

EXAMPLE 7

3-Phenyl-1,2-diaminopropane 3. A solution of 2 (18.25 g, 0.125 mol) in dichloromethane (150 mL) was added over 30 min to a 1M solution diisobutylaluminum hydride of DIBAL (500 mL, 0.5 mol) cooled to −10°. The temperature raised to −5° and returned to −10°. The starting material was gone after 15 min (GC). The cooled reaction mixture was treated with 500 mL of aqueous 2N sodium hydroxide at a rate, which kept the temperature under 20°. The resulting mixture was stirred at room temperature for 1 hr and then it was filtered through 1PS filter paper. The solvent was evaporated under reduced pressure and the residue was distilled through a short path column to give 12.7 g (68% yield) of 3-phenyl-1,2-diamino-propane, 3 (b.p. 78–83° C., 0.2–0.3 mm) which was 90% pure by glpc. NMR (CDCl$_3$) δ 7.4 (s, 5H), 2.4–3.2 (m, 5H), 1.4 (s, 4H).

EXAMPLE 8

3-Methyl-3-phenyl-1,2-diaminopropane 11, NMR (CDCl$_3$) δ 7.4(S, 5H), 2.2–3.1(m, 4H), 1.1–1.5(m, 7H), was prepared as described above (42% yield) bp 90–93° C. (0.4 mm).

EXAMPLE 9

2-(Cyclohex-1-enyl)-1,2-diaminoethane 18E, NMR (CDCl$_3$) δ 5.7(S br, 1H), 3.1–3.4(m, 1H), 2.6–2.8(m, 2H), 1.9–2.3(m, 4H), 1.4–1.8(m, 4H), 1.2(S, 4H), was prepared as described above (42% yield). bp 74–78° C. (1 mm).

EXAMPLE 10

3-Ethyl-1,2-diaminopentane 18F, NMR (CDCl$_3$) δ 2.5–2.8(m, 3H), 0.6–1.6(m,15H), was prepared as described above (65% yield). bp 46–49° C. (1 mm).

EXAMPLE 11

3-Methyl-1,2-diaminopentane 18G, NMR (CDCl$_3$) δ 2.4–3.0(m, 3H), 0.7–1.8(m, 13H), was prepared as described above (42% yield). bp 41–44° C. (5 mm).

EXAMPLE 12

3-(S)-3-Methyl-1,2-diaminopentane 18H, NMR (CDCl$_3$) δ 2.4–3.0(m, 3H), 0.7–1.8(m, 13H), was prepared as described above (42% yield). bp 42–44° C. (3 mm).

EXAMPLE 13

2-Phenyl-1,2-diaminoethane 27, NMR (CDCl$_3$) δ 7.35(S, 5H), 3.8–4.2(t, 1H), 2.7–3.1(m,2H), 1.4(S, 4H), was prepared from aminonitrile 26 as described above (41% yield). bp 76–80° C. (0.5 mm). Aminonitrile 26 was prepared in 85% yield from commercially available 2-phenyl-2-aminoacetonitrile hydrochloride by treatment with aqueous ammonia and extraction with dichloromethane. NMR (CDCl$_3$) δ7.4–7.8(m, 5H), 5.0(S br, 1H), 2.1(S br, 2H).

EXAMPLE 14

2-Phenyl-1,2-diaminoethane 27 from 24. To a solution of N-methoxy[2-nitro-1-(2-phenyl)]ethylamine 24 (9.8 g, 0.05 mol) in ethanol (100 mL) was added 10% Pd/C (4 g) and hydrogenated at 34 psi for 4 hr. The reaction mixture was filtered through a pad of celite (2 g). The pad was washed with ethanol (15 mL). The filtrate was concentrated under reduced pressure to give 6.4 g (94% yield) of 27 as light yellow oil.

2-Furyl-1,2-diaminoethane 35I. In a 500 mL 3-necked flask equipped with a condenser, stir-bar and a thermometer was placed N-methoxy[2-nitro-1-(2-furyl]ethylamine 34I (9.3 g, 0.05 mol) in acetic acid (175 mL). Zinc dust (39 g, 0.6 mol) was added in four portions with cooling in a water-bath to maintain an internal temperature about 55° C. The reaction mixture was refluxed for 1 hr and then was cooled to room temperature. The resulting mixture was filtered and filter paper was washed with acetic acid (150 mL). The filtrate was concentrated under reduced paper. The residue was dissolved in dichloromethane (100 mL) and to this solution was added very slowly a solution of 20% NaOH (150 mL) with cooling. The resulting mixture was stirred for 15 min. The aq. layer was separated and extracted with 25% IPA/dichloromethane (3×50 mL). The combined organic layers were washed with 20% NaOH solution (1×50 mL), brine (1×50 mL), filtered, and concentrated under reduced pressure to give 5.0 g of the crude product. Distillation through a short path still gave 2.5 g (40% yield) of 2-furyl-1,2-diaminoethane, 35I, bp 58–68° C. (0.6 mm) which was 100% pure by GC. NMR (CDCl$_3$) δ 7.5–7.7(m, 1H), 6.3–6.6 (m, 2H), 4.0(t, 1H), 2.9–3.2(m, 2H), 1.5(S br, 4H).

EXAMPLE 16

2-Thienyl-1,2-diaminoethane 35J, NMR (CDCl$_3$) δ 7.0–7.5(m, 3H), 4.3(t, 1H), 3.0(dd, 2H), 1.5(S, 4H), was prepared as described above (50%), bp 78–82° C. (0.5 mm).

EXAMPLE 17

4-Benzyl-2-imidazolidinethione 4. A solution of 3 (9.75 g, 0.65 mol) in dichloromethane (75 mL) under argon was treated with a solution of 1,1'-thiocarbonyldiimidazole in dichloromethane (12.16 g, 0.068 mol) added over 45 min. The reaction was stirred for 15 min after the addition was complete and HPLC analysis indicated complete reaction. The reaction mixture was diluted with dichloromethane (200 mL) and washed with water (3×100 mL) and brine (100 mL). The organic solution was filtered through 1PS filter paper and evaporated under reduced pressure to give a yellow solid. The solid was suspended in 100 mL of 10% hexane-ethyl acetate and filtered. The filter cake was washed with 50 mL of 10% hexane-ethyl acetate and air dried to give 11.2 g (90% yield) of 4. HPLC analysis indicated 99% purity. NMR (CDCl$_3$:d$_6$-DMSO) δ 7.8 (S br, 2H), 7.4 (S, 5H), 4.0–4.7 (m, 1H), 3.3–3.9 (m, 2H), 2.7–3.2 (m, 2H).

EXAMPLE 18

4-(1-Phenylethyl)-2-imidazolidinethione 12, NMR (CDCl$_3$:d$_6$-DMSO) δ 8.3(S br, 1H), 7.9(S br, 1H), 7.5(S, 5H), 2.7–4.4(m, 4H), 1.4(two d, 3H), was prepared as described above (82%).

EXAMPLE 19

4-(Cyclohex-1-enyl)-2-imidazolidinethione 19E, NMR (CDCl$_3$) δ 7.4(S br,1H), 7.2(S br, 1H), 5.8(S br, 1H), 4.4–4.8(m, 1H), 3.4–4.2(m, 2H). 1.8–2.3(m, 4H), 1.4–1.8 (m, 4H), was prepared as described above (79% yield).

EXAMPLE 20

4-(2-Ethylpropyl)-2-imidazolidinethione 19F, NMR CD$_3$OD δ 7.3–7.6(d br, 2H), 3.3–4.4(m, 3H), 1.2–1.7(m, 5H), 0.6–1.2(m, 6H), was prepared as described above (81% yield).

EXAMPLE 21

4-(2-Butyl)-2-imidazolidinethione 19G, NMR (CDCl$_3$) δ 7.2–7.8(d br, 2H), 3.4–4.3(m, 3H), 0.7–1.9(m, 9H), was prepared as described above (76% yield).

EXAMPLE 22

(S)-4-(2-Butyl)-2-imidazolidinethione 19H, NMR (CDCl$_3$) δ 7.3–7.7(d br,2H), 3.4–4.3(m, 3H), 0.6–1.9(m, 9H), was prepared as described above (68% yield).

EXAMPLE 23

4-Phenyl-2-imidazolidinethione 28, NMR (CDCl$_3$:d$_6$-DMSO) δ 8.6(S br, 1H), 8.2(S br, 1H), 7.4(S, 5H), 4.8–5.2 (m, 1H), 3.84–4.3(t, 1H), 3.2–3.6(m, 1H), was prepared as described above (88% yield).

EXAMPLE 24

4-(2-Furyl)-2-imidazolidinethione 36I, NMR (CDCl$_3$:d$_6$-DMSO) δ 8.4(S br, 1H), 8.2(S br, 1H), 7.7(m, 1H), 6.5(m, 2H), 5.0–5.4(m, 1H), 3.6–4.3(m, 2H), was prepared as described above (58% yield).

EXAMPLE 25

4-(2-Thienyl)-2-imidazolidinethione 36J, Method 1. NMR (CDCl$_3$:d$_6$-DMSO) δ 8.7(S br, 1H), 8.2(S br, 1H), 7.4–7.6(m, 1H), 7.0–7.2(m, 2H), 5.2–5.6(m, 1H), 3.4–4.4 (m, 2H), was prepared as described above (78% yield).

EXAMPLE 26

4-(2-Thienyl)-2-imidazolidinethione 36J, Method 2 . . . A solution of 140 mg (1.0 mmol) of 2-thienyl-1,2-diaminoethane and allyl isothiocyanate (99 mg, 1 mmol) in bromobenzene (5 mL) was heated for 40 min and allowed to cool to room temperature and then cooled to −5° C. The title compound (160 mg, 83% yield) was obtained upon filtration and washing with hexane.

EXAMPLE 27

The same procedure applied to 1,2-diaminoethane afforded 2-imidazolidinethione in 91% yield.

NBS oxidation of 4. Thione 4 (0.176 g, 9.0 mmol) in 15 mL of acetonitrile was treated with a solution of NBS (0.196 g, 1.1 mmol) in 5 mL of acetonitrile added over 15 min. The solution turned yellow and some solid precipitated. The solvent was stripped after hplc indicated the reaction was complete. The residue was dissolved in dichloromethane (50 mL) and the solution was extracted with water (2×20 mL). The solution was evaporated under reduced pressure to give a foam (0.1 g). The foam was triturated with 10 mL of 2:1 ethyl acetate-hexane and the solid was collected to give 72 mg of 8. The aqueous layer was further extracted with 30% isopropanol-dichloromethane and the extracts were processed to give another 40 mg of additional material bringing the yield to 112 mg (ca 63%). The mass spectrum showed the parent ion at 350 mass units consistent with structure 8. NMR (CDCl$_3$: CD$_3$OD) δ 7.5 (s, 5H), 4.2–4.8 (m, 2H), 3.5–4.1 (m, 2H), 2.8–3.4 (m, 2H).

EXAMPLE 28

4-Methoxybenzylthioether hydrochloride 5A. Imidazolidine-2-thione 4 (2.3 g, 0.012 mol) and p-methoxybenzyl chloride (2.35 g, 0.015 mol) in ethanol (25 mL) was heated under reflux for 2 hr when the reaction was complete by hplc. The ethanol was evaporated under reduced pressure and the residue was triturated twice with 25 mL of 1:1 ethyl acetate-hexane. The remaining solid weighed 4.0 g (96% yield) after drying in the air. The material was 95% pure by hplc. NMR (CDCl$_3$) δ 11.4 (s br, 1H), 10.8 (s br, 1H), 6.8–7.6 (m, 9H), 4.7 (s br, 2H), 3.9 (s, 3H), 2.6–3.85 (m, 3H).

EXAMPLE 29

4-Methoxybenzylthioether hydrochloride 13, NMR (CDCl$_3$) δ 10.3–11.3(s br, 2H), 6.8–7.8(m, 9H), 4.6(S br, 2H), 3.2–4.1(m, 7H), 1.1–1.7(m, 3H), was prepared as described above (100% yield).

EXAMPLE 30

4-Acetoxybenzylthioether hydrochloride 5B, NMR (CDCl$_3$) δ 11.2 (s br, 1H), 10.9 (s br, 1H), 6.8–7.6 (m, 9H), 4.7 (s br, 2H), 2.6–4.0 (m, 5H), 2.3 (s, 3H), was prepared by using 4-acetoxybenzyl chloride as described above (96% yield).

EXAMPLE 31

4-Benzylthioether hydrochloride 5C, NMR (CDCl$_3$:d$_6$-DMSO) δ 10.1 (s br, 2H), 7.6 (s, 5H), 7.5 (s, 5H), 4.8 (s, 2H), 3.5–4.2 (m, 3H), 2.7–3.3 (m, 2H), was prepared by using benzyl chloride as described above (92% yield).

EXAMPLE 32

Allyl thioether hydrochloride 5D. Imidazolidine-2-thione 4 (9.6 g, 0.05 mol) and allyl chloride (25 mL) in ethanol (100 mL) was heated under reflux for 3 hr when the reaction was complete by hplc. The reaction mixture was concentrated under reduced pressure and the residue was triturated with ether (50 mL). The remaining solid weighed 12.9 g (96% yield) after drying under reduced pressure. The material was 98% pure by hplc. NMR (CD$_3$OD) δ 7.4(S, 5H), 5.2–6.4(m, 4H), 4.5–4.8(m, 1H), 3.6–4.2(m, 4H), 3.0(d, 2H).

EXAMPLE 33

Allyl thioether hydrochloride 20E, NMR (CDCl$_3$) δ 11.6–12.2(S br,2H), 5.3–6.3(m, 4H), 4.6–5.0(m, 1H), 3.6–4.4(m, 4H), 1.8–2.3 (m, 4H), 1.4–1.8(m, 4H), was prepare as described above (100% yield).

EXAMPLE 34

Allyl thioether hydrochloride 20F, NMR (CD$_3$OD) δ 5.2–6.4(m, 3H), 3.6–4.4(m, 5H), 0.6–1.7(m, 13H), was prepare as described above (100% yield).

EXAMPLE 35

Allyl thioether hydrochloride 20G, NMR (CDCl$_3$) δ 10.6–11.5(S br, 2H), 5.2–6.4(m, 3H), 3.4–4.5(m, 5H), 0.6–2.2(m, 9H), was prepare as described above (100% yield).

EXAMPLE 36

Allyl thioether hydrochloride 20H, NMR (CDCl$_3$) δ 10.6–11.5(d br, 2H), 5.2–6.2(m, 3H), 3.4–4.4(m, 5H), 0.6–2.0(m, 9H), was prepare as described above (68% yield).

EXAMPLE 37

Allyl thioether hydrochloride 29, NMR (CD$_3$OD) δ 7.6(S, 5H), 5.3–6.4(m, 4H), 5.5(S br, 2H), 3.7–4.8(m, 4H), was prepare as described above (100% yield).

EXAMPLE 38

Allyl thioether hydrochloride 37I, NMR (CDCl$_3$) δ 10.3(S br, 2H), 7.5–7.6(m, 1H), 6.5–6.7(m, 2H), 5.2–6.1(m, 4H), 4.0–4.4(m, 4H), was prepare as described above (96% yield).

EXAMPLE 39

Allyl thioether hydrochloride 37J, NMR (CDCl$_3$) δ 11.8(S br, 1H), 11.3(S br, 1H), 7.0–7.8(m, 3H), 5.3–6.0(m, 4H), 3.6–4.6(m, 4H) was prepare as described above (100% yield).

EXAMPLE 40

4-Benzyl-2-(4-methoxybenzyl)imidazolethioether 6A. In a 100 mL 3-necked flask equipped with a thermometer, a dropping funnel, a drying tube, and stir-bar was placed oxalyl chloride (7 mL of 2 M solution in dichloromethane, 0.014 mol) in 15 mL of dichloromethane. The solution was stirred and cooled to −50° C. A solution of dimethyl sulfoxide (2.19 g, 0.028 mol) in 15 mL of dichloromethane was added over 20 min. The resulting mixture was stirred at −50° C. for 30 min and then a solution of thioether hydrochloride 5A (3.83 g, 0.011 mol) in 20 mL of dichloromethane was added over 30 min. After stirring for an additional 15 min at −50° C., the reaction was complete by hplc. To the reaction mixture was added triethylamine (5.56 g, 0.055 mol) in one portion and after 15 min, the cooling bath was removed. The resulting mixture was stirred at room temperature for 60 min, diluted with 50 mL dichloromethane, washed with water (2×50 mL), brine (1×50 mL), filtered through 1PS filter paper and concentrated under reduced pressure to give 3.85 g of an oil. The oil was flash chromatographed on a 75 g flash chromatography silica gel with 10 g of anhydrous sodium sulfate on top. The column was eluted with 100 mL portions of 20% ethyl acetate in hexane for fractions 1–5, 30% ethyl acetate in hexane for fractions 6–15, and 40% ethyl acetate in hexane for fractions 16–20. The product eluted in fractions 9–17 (TLC solvent: 50% ethyl acetate/hexane) to give 2.8 g (82% yield) of 6A as a yellow oil. The material was 95% pure by hplc. NMR (CDCl$_3$) δ 7.4 (s, 5H), 6.8–7.35 (m, 5H), 4.2 (s, 2H), 4.1 (s, 2H), 3.8 (s, 3H).

EXAMPLE 41

Imidazolethioether 6B, NMR (CDCl$_3$) δ 10.6 (s br, 1H), 7.4 (s, 5H), 6.8–7.4 (AB q, 4H), 6.7 (s, 1H), 4.2 (s, 2H), 4.0 (s, 2H), 2.3 (s, 3H), was prepared as described above (65% yield).

EXAMPLE 42

Imidazolethioether 6C, NMR (CDCl$_3$) δ 10.9 (s br, 1H), 7.4 (s, 5H), 7.3 (s, 4H), 6.75 (s, 1H), 4.2 (s, 2H), 3.9 (s, 2H), was prepared as described above (66% yield).

EXAMPLE 43

Imidazolethioether 14, NMR (CDCl$_3$) δ 12.5(S br, 1H), 6.8–7.5(m, 10H), 4.0–4.4(m, 3H), 3.75(S, 3H), 1.7(d, 3H), was prepared as described above (78% yield).

EXAMPLE 44

Imidazolethioether 21E, NMR (CDCl$_3$, CD$_3$OD) δ 7.0(s, 1H), 6.3(t br, 1H), 5.6–6.2(m, 1H), 5.0–5.3(m, 2H), 4.9(s, 1H), 3.8(d, 2H), 2.0–2.6(m, 4H), 1.4–2.0(m, 4H), was prepared as described above (64% yield).

EXAMPLE 45

Imidazolethioether 21F, NMR (CDCl$_3$) δ 12.4(S br, 1H), 7.0(S, 1H), 5.5–6.4(m, 1H), 4.9–5.3(m, 2H), 3.6(d, 2H), 2.4–2.8(m, 1H), 1.4–2.0(m, 4H), 0.8(t, 6H), was prepared as described above (87% yield).

EXAMPLE 46

Imidazolethioether 21G, NMR (CDCl$_3$) δ 12.1(S br, 1H), 7.0(s, 1H), 5.7–6.6(m, 1H), 5.0–5.4(m, 2H), 3.6(d, 2H), 2.6–3.2(m, 1H), 1.5–2.1(m, 2H), 1.3(d, 3H), 0.9(t, 3H), was prepared as described above (86% yield).

EXAMPLE 47

Imidazolethioether 21H, NMR (CDCl$_3$) δ 12.4(S br, 1H), 7.0(s, 1H), 5.7–6.6(m, 1H), 5.0–5.4(m, 2H), 3.6(d, 2H), 2.6–3.2(m, 1H), 1.5–2.1(m, 2H), 1.3(d, 3H), 0.9(t, 3H), was prepared as described above (82% yield).

EXAMPLE 48

Imidazolethioether 30, NMR (CDCl$_3$) δ 12.2(S, 1H), 7.7–8.0(m, 2H), 7.2–7.7(m, 4H), 5.6–6.4(m, 1H), 4.9–5.2 (m, 2H), 3.7(d, 2H) was prepared as described above. The crude product was triturated with 10% EtOAc/Hexane (4×25 mL) to give 30 in 79% yield.

EXAMPLE 49

Imidazolethioether 38I NMR (d$_6$-DMSO) δ 7.7–7.9(m. 1H), 7.6(S, 1H), 6.7–6.9(m, 2H), 5.7–6.4(m,1H), 5.1–5.6(m, 2H), 3.7–4.1(d, 2H), was prepared as described above (81% yield).

EXAMPLE 50

Imidazolethioether 38J NMR (CDCl$_3$:d$_6$-DMSO) δ 7.1–7.8(m, 4H), 5.7–6.6(m, 1H), 5.3(t br, 2H), 3.8(d br,2H), was prepared as described above (70% yield).

EXAMPLE 51

4-Benzylimidazole-2-thione 7. Method 1. Imidazolethioether 6A (0.124 g, 0.0004 mol) in 5 mL of trifluoroacetic acid was refluxed for 48 hr. The reaction mixture was diluted with 5 mL of dichloromethane and concentrated under reduced pressure. The resulting residue was triturated with 5 mL of dichloromethane and placed in a freezer for 30 min. The white solid was collected and air dried to give 0.039 g (51% yield) of 7. Hplc analysis showed a purity of 99%. NMR (CD$_3$OD) δ 7.4 (s, 5H), 6.6 (s, 1H), 4.8 (s br, 2H), 3.8 (s, 2H).

EXAMPLE 52

4-Benzylimidazole-2-thione 7. Method 2. Imidazolethioether 6A (0.31 g, 0.001 mol) in 5 mL of dichloromethane was treated with 3.5 mL of methanesulfonic acid at room temperature for 48 hr and refluxed for 3 hr. The reaction mixture was worked-up as above and gave 0.95 g (50% yield) of 7.

EXAMPLE 53

4-(1-Phenylethyl)imidazole-2-thione 15, NMR (d$_6$-DMSO) δ 9.1(S br, 2H), 7.4(S, 5H), 6.6(S, 1H), 3.9–4.4(m, 1H), 1.5(d, 3H), was prepared as described in method 1 (78% yield).

EXAMPLE 54

4-Benzylimidazole-2-thione 7 from imidazolethioallylether 6D. To a solution of imidazolethioether 6D (0.115 g, 0.0005 mol) in dichloromethane (5 mL) was added p-toluenesulfonic acid (0.086 g, 0.00055 mol) followed by addition of tetrakis (triphenylphosphine)palladium (0.021 g, 0.000175 mol). The resulting mixture was stirred at room temperature. After 15 min, the product was started to form as a white solid. After 1 hr, the solid was collected and air dried to give 0.067 g (70% yield) of 7. Hplc analysis showed a purity of 99%.

EXAMPLE 55

4-(1-Cyclohexenyl)imidazole-2-thione, 7E, was prepared from 21E as described above after collecting the product from reaction mixture and column chromatography of the filtrate over flash silica gel using 20 to 30% ethyl acetate/hexane (67% yield). NMR (CDCl$_3$:d$_6$-DMSO) δ 12.0–12.8(d br, 2H), 6.7(S, 1H), 6.4(s, 1H), 2.0–2.6(m, 4H), 1.6–2.2(m, 4H).

EXAMPLE 56

4-(3-Pentanyl)imidazole-2-thione, 7F, was prepared from 21F as described above by flash column chromatography using 50% ethyl acetate/hexane (76% yield). NMR (CDCl$_3$) δ 12.8(S br, 2H), 6.6(S, 1H), 2.2–2.7(m, 1H), 1.5–2.0(m, 4H), 0.6–1.2(t, 6H).

EXAMPLE 57

4-(2-Butyl)imidazole-2-thione, 7G, was prepared from 21G as described above by flash column chromatography using 25% ethyl acetate/hexane (66%). NMR (CDCl$_3$) δ 12.2–12.8(d br, 2H), 6.6(S, 1H), 2.2–3.0(m, 1H), 0.6–2.0(m, 8H).

EXAMPLE 58

(S)-4-(2-Butyl)imidazole-2-thione, 7H, was prepared from 21H as described above by flash column chromatography using 30% ethyl acetate/hexane (40% yield). Its NMR is the same as 7G.

EXAMPLE 59

4-(2-Furyl)imidazole-2-thione, 7I, was prepared from 38I as described above (78% yield). NMR 300 MHz, (CDCl$_3$:d$_6$-DMSO) δ 7.15(S, 1H), 6.6(S, 1H), 6.5(d, 1H), 6.2(m, 1H).

4-(2-Thienyl)imidazole-2-thione, 7J, was prepared from 38J as described above (10% yield). NMR 300 MHz, (d$_6$-DMSO) δ 12.7(S, 1H), 12.2(S, 1H), 6.9–7.6(m, 4H).

EXAMPLE 60

4-Phenylimidazole-2-thione, 31, was prepared from 30 as described above. NMR (CDCl$_3$:d$_6$-DMSO) δ 12.7(S br, 1H), 12.3(S br, 1H), 7.7–8.0(m, 2H), 7.2–7.7(m, 4H).

EXAMPLE 61

2-(2-Nitrovinyl)furan 33I. In a 1L 3-necked flask equipped with a mechanical stirrer, thermometer and a dropping funnel was placed 2-furaldehyde 32I (48 g, 0.5 mol) and nitromethane (30.5 g, 0.5 mol) in methanol (100 mL). The resulting mixture was cooled to −5° C. A solution of sodium hydroxide (21 g, 0.525 mol) in water (75 mL) was added at such a rate to maintain internal temperature at 0° C. (45 min). The resulting paste was stirred at 0° C. for 1 hr and then ice cold water (100 mL) was added to get a homogeneous mixture. This mixture was poured into a stirring cold solution of hydrochloric acid (100 mL of concentrate hydrochloric acid in 150 mL of water)over 20 min. After 30 min, yellow solid was collected, washed with water (250 mL) and treated with 2 g of charcoal (Norit A) in boiling ethanol (75 mL). Hot filtered through a pad of celite (7 g) in a steam jacketed Buchner funnel. The pad was washed with hot ethanol (15 mL). The filtrate was placed in a fridge for 1 hr and then yellow solid was collected and air dried to give 44 g (63% yield) of 33I. Hplc analysis showed a purity of 98%. NMR (CDCl$_3$) δ 7.8(q, 2H), 7.8(S br, 1H), 7.1(d, 1H), 6.7–6.9(m, 1H).

EXAMPLE 62

2-(2-nitrovinyl)thiophene 33J was prepared as described above (63% yield). NMR (CDCl$_3$) δ 7.3–8.5(m).

EXAMPLE 63

Nitrostyrene 23 was made according to known literature[5] in 83% yield. NMR (CDCl$_3$) δ 7.9(dd, 2H), 7.7(S, 5H).

EXAMPLE 64

2-Nitro-1-phenyl-N-methoxyethylamine 24. To a solution of nitrostyrene 23 (14.9 g, 0.1 mol) in tetrahydrofuran (100 mL) was added solid O-methylhydroxylamine hydrochloride (9.2 g, 0.11 mol) and sodium hydrogen carbonate (9.24 g, 0.11 mol). The reaction mixture was diluted with water (25 mL) and stirred at room temperature overnight under argon. The reaction mixture was mixed with ethyl acetate (150 mL) and washed with water (1×50 mL). The aqueous layer was back washed with ethyl acetate (1×50 mL). The combined organic layers were washed with brine (1×75 mL), filtered through 1PS filter paper and stripped to give 18.6 g (95% yield) of 34I as brown oil. Hplc analysis showed a purity of 98%. NMR (CDCl$_3$) δ 7.5(S, 5H), 6.1(S br, 1H), 4.5–5.1(m, 3H), 3.5(S, 3H).

EXAMPLE 65

2-Nitro-1-(2-furyl)-N-methoxyethylamine, 34I, was prepared as described above (100% yield). NMR (CDCl$_3$) δ 7.5–7.6(m, 1H), 6.5–6.6(m, 2H), 6.2(S br, 1H), 4.7–5.2(m, 3H), 3.6(S, 3H).

EXAMPLE 66

2-Nitro-1-(2-thienyl)-N-methoxyethylamine, 34J, was prepared as described above (100% yield). NMR (CDCl$_3$) δ 7.0–7.5(m, 3H), 6.1(S br, 1H), 4.6–5.3(m, 3H), 3.6(S, 3H).

In particular, various reaction conditions, including temperatures, pressures, solvents, catalyst, etc. may be substituted for those shown in the Examples by those skilled in the art.

While particular embodiments of the invention have been described it will be understood of course that the invention is not limited thereto since many obvious modifications can be made and it is intended to include within this invention any such modifications as will fall within the scope of the appended claims.

What is claimed is:

1. A method of making an imidazole-2-thione which comprises the steps of reacting a vicinal diamine having the formula I $$R-CH(NH_2)-CH(R^1)-NH_2$$

wherein R is selected from the group consisting of hydrogen, alkyl, alkenyl, alkoxy, carbocyclic aryl and heterocyclic aryl radicals and $R^1$ is selected from the group consisting of hydrogen, alkyl, alkoxy, carbocyclic aryl and heterocyclic aryl, radicals with a compound having a thiocarbonyl moiety to obtain a first reaction product having the general formula II

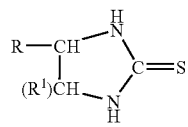

reacting said first reaction product with $R^3$—Cl to provide a second reaction product having the formula IV

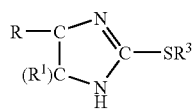

wherein $R^3$ is selected from the group consisting of allyl, benzyl, 2, 4 dimethoxybenzyl, 2-methoxy benzyl and acetoxy benzyl and oxidizing said reaction product to obtain an imidazole-2-thione having the formula III

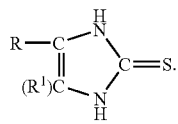

2. The method of claim 1 wherein $R^1$ is H.

3. The method of claim 1 wherein said compound having a thiocarbonyl moiety is selected from the group consisting of 1, 1'thiocarbonyl diimidazole and allylisothiocyanate.

4. The method of claim 1 wherein $R^3$ is selected from the group consisting of 4-methoxybenzyl, 4-acetoxybenzyl and allyl.

5. The method of claim 4 wherein R is selected from the group consisting of hydrocarbyl radicals having from one to twenty carbon atoms and single ring heteroaryl radicals wherein the heteroatom is selected from the group consisting of oxygen and sulfur.

6. The method of claim 4 wherein R is selected from the group consisting of alkyl, aryl, alkenyl, furyl and thienyl radicals.

7. The method of claim 4 wherein R is selected from the group consisting of benzyl, phenyl, phenylethyl cyclohexene, 3-pentyl, 2-pentyl, buxtyl, 2-furyl and 2-thienyl.

8. The method of claim 1 wherein said vicinal diamine is prepared by reacting a compound of formula V

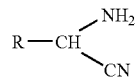

wherein R is selected from the group consisting of hydrogen, alkyl, alkenyl, carbocyclic aryl and heterocyclic aryl radicals with nitromethane to obtain a reaction product of formula VIII $$R—CH=CH—NO_2$$

and said reaction product of formula VIII is reacted with O-methylhydroxylamine to obtain a reaction product of formula IX

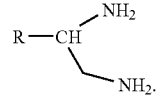

and said reaction product of formula IX is reduced to a vicinal diamine having the formula VII

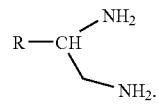

* * * * *